(12) United States Patent
Bauer

(10) Patent No.: US 8,221,707 B2
(45) Date of Patent: Jul. 17, 2012

(54) PROCESS FOR ISOMERIZING A NON-EQUILIBRIUM ALKYLAROMATIC FEED MIXTURE AND AN AROMATIC PRODUCTION FACILITY

(75) Inventor: John E. Bauer, LaGrange Park, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/041,930

(22) Filed: Mar. 7, 2011

(65) Prior Publication Data

US 2011/0158859 A1    Jun. 30, 2011

Related U.S. Application Data

(62) Division of application No. 11/954,462, filed on Dec. 12, 2007, now Pat. No. 7,932,426.

(51) Int. Cl.
*B01J 8/00* (2006.01)
*B01J 8/04* (2006.01)
*C07C 5/27* (2006.01)

(52) U.S. Cl. ........ 422/600; 422/608; 422/620; 422/622; 422/630; 422/631; 585/477; 585/478

(58) Field of Classification Search .......... 422/600, 422/608, 620, 622, 630, 631; 585/477, 478
See application file for complete search history.

(56) References Cited

U.S. PATENT DOCUMENTS

| | | | | |
|---|---|---|---|---|
| 3,835,198 A | * | 9/1974 | Myers | 585/479 |
| 6,660,896 B1 | * | 12/2003 | Buchanan et al. | 585/481 |

\* cited by examiner

*Primary Examiner* — Jennifer A Leung
(74) *Attorney, Agent, or Firm* — Mark R. Willis

(57) ABSTRACT

One exemplary embodiment can be a process for the isomerization of a non-equilibrium alkylaromatic feed mixture. The process can include contacting the non-equilibrium alkylaromatic feed mixture in a C8 isomerization zone. The C8 isomerization zone may include a first isomerization stage and a second isomerization stage. At the first isomerization stage, at least a portion of the non-equilibrium alkylaromatic feed mixture can be contacted at a first isomerization condition in a liquid phase in the substantial absence of hydrogen to obtain an intermediate stream. At the second isomerization stage, at least part of the intermediate stream and at least a part of a stream rich in at least one naphthene can be contacted at a second isomerization condition to obtain a concentration of at least one alkylaromatic isomer that is higher than a concentration of that at least one alkylaromatic isomer in the non-equilibrium feed mixture.

1 Claim, 1 Drawing Sheet

PROCESS FOR ISOMERIZING A NON-EQUILIBRIUM ALKYLAROMATIC FEED MIXTURE AND AN AROMATIC PRODUCTION FACILITY

CROSS-REFERENCE TO RELATED APPLICATION

This application is a Division of application Ser. No. 11/954,462 which was filed Dec. 12, 2007, now allowed, the contents of which are incorporated herein by reference thereto.

FIELD OF THE INVENTION

The field of this invention generally relates to a process for isomerizing a non-equilibrium alkylaromatic feed mixture and/or an aromatic production facility that, at least in part, may isomerize a non-equilibrium alkylaromatic feed mixture.

BACKGROUND OF THE INVENTION

The xylenes, such as para-xylene, meta-xylene and ortho-xylene, can be important intermediates that find wide and varied application in chemical syntheses. Generally, paraxylene upon oxidation yields terephthalic acid that is used in the manufacture of synthetic textile fibers and resins. Meta-xylene can be used in the manufacture of plasticizers, azo dyes, and wood preservers. Generally, ortho-xylene is a feedstock for phthalic anhydride production.

Xylene isomers from catalytic reforming or other sources generally do not match demand proportions as chemical intermediates, and further comprise ethylbenzene, which can be difficult to separate or to convert. Typically, para-xylene is a major chemical intermediate with significant demand, but amounts to only 20-25% of a typical C8 aromatic stream. Adjustment of an isomer ratio to demand can be effected by combining xylene-isomer recovery, such as adsorption for para-xylene recovery, with isomerization to yield an additional quantity of the desired isomer. Typically, isomerization converts a non-equilibrium mixture of the xylene isomers that is lean in the desired xylene isomer to a mixture approaching equilibrium concentrations. It is also desirable to convert ethylbenzene to one or more xylenes while minimizing xylene loss. Moreover, other desired aromatic products, such as benzene, can be produced from such processes.

Various catalysts and processes have been developed to effect xylene isomerization. In one such system, isomerization can include separate reactors having different functions. Particularly, one reactor having a first isomerization catalyst can perform xylene isomerization with low ethylbenzene conversion, while the other reactor having a second isomerization catalyst may perform ethylbenzene conversion with low xylene isomerization. If the ethylbenzene reactor can selectively convert ethylbenzene into one of the xylene isomers, typically para-xylene, then above-equilibrium levels of the preferred isomer can be obtained. Depending on the isomerization catalyst, the ethylbenzene may also be converted to xylenes, or may simply be dealkylated. In this way, the desired product yield is maximized by converting the undesired components. Yield is greatest when undesired products can be minimized and ethylbenzene conversion can be maximized.

One way to reduce loss of cyclic hydrocarbons having eight carbon atoms (hereinafter may be abbreviated as "C8 ring loss" or "C8RL") is to operate in a liquid phase. In the absence of hydrogen, saturation and cracking reactions may be essentially eliminated.

Generally, C8 naphthenes are intermediates for an ethylbenzene conversion bed in the isomerization of ethylbenzene to xylenes. Typically, C8 naphthenes are not intermediates for xylene isomerization, although the C8 naphthenes may be included in the feed to the xylene isomerization zone. Alternatively, if the ethylbenzene level is very low or zero, only the xylene isomerization may be required.

Thus, it would be desirable to improve the operation of the liquid-phase xylene isomerization by altering the feed to reduce C8RL while increasing isomerization activity.

BRIEF SUMMARY OF THE INVENTION

One exemplary embodiment can be a process for the isomerization of a non-equilibrium alkylaromatic feed mixture. The process can include contacting the non-equilibrium alkylaromatic feed mixture in a C8 isomerization zone. The C8 isomerization zone may include a first isomerization stage and a second isomerization stage. At the first isomerization stage, at least a portion of the non-equilibrium alkylaromatic feed mixture can be contacted at a first isomerization condition in a liquid phase in the substantial absence of hydrogen to obtain an intermediate stream. At the second isomerization stage, at least part of the intermediate stream and at least a part of a stream rich in at least one naphthene can be contacted at a second isomerization condition to obtain a concentration of at least one alkylaromatic isomer that is higher than a concentration of that at least one alkylaromatic isomer in the non-equilibrium alkylaromatic feed mixture.

Another exemplary embodiment can be a process for the isomerization of a non-equilibrium alkylaromatic feed mixture. The process can include contacting the non-equilibrium alkylaromatic feed mixture in a C8 isomerization zone. The C8 isomerization zone may include a first isomerization stage and a second isomerization stage. At the first isomerization stage, at least a portion of the non-equilibrium alkylaromatic feed mixture is contacted at a first isomerization condition in a liquid phase in the substantial absence of hydrogen to obtain an intermediate stream. At the second isomerization stage, at least part of the intermediate stream and all of a stream comprising substantially at least one naphthene may be contacted at a second isomerization condition to obtain a concentration of at least one alkylaromatic isomer that is higher than a concentration of that at least one alkylaromatic isomer in the non-equilibrium alkylaromatic feed mixture.

A further exemplary embodiment can be an aromatic production facility. The aromatic production facility can include a xylene isomer separation zone, a C8 aromatic isomerization zone receiving a non-equilibrium alkylaromatic feed mixture from the xylene isomer separation zone, and a separation zone for obtaining at least part of a stream rich in at least one naphthene. The C8 aromatic isomerization zone may further include first and second isomerization stages. At the first isomerization stage, at least a portion of the non-equilibrium alkylaromatic feed mixture is contacted at a first isomerization condition in a liquid phase in the substantial absence of hydrogen to obtain an intermediate stream. At a second isomerization stage, at least part of the intermediate stream and at least part of a stream rich in at least one naphthene from the separation zone may be contacted at a second isomerization condition to obtain a concentration of at least one alkylaromatic isomer that is higher than a concentration of that at least one alkylaromatic isomer in the non-equilibrium alkylaromatic feed mixture.

Therefore, the process and/or aromatic production facility can improve activity, selectivity, and stability. Particularly, the process can provide increased isomerization of xylenes while minimizing C8RL.

DEFINITIONS

As used herein, the term "zone" can refer to an area including one or more equipment items and/or one or more sub-zones. Equipment items can include one or more reactors or reactor vessels, heaters, separators, exchangers, pipes, pumps, compressors, and controllers. Additionally, an equipment item, such as a reactor or vessel, can further include one or more zones or sub-zones.

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals. The stream can also include aromatic and non-aromatic hydrocarbons. Moreover, the hydrocarbon molecules may be abbreviated C1, C2, C3 . . . Cn where "n" represents the number of carbon atoms in the hydrocarbon molecule.

As used herein, the term "aromatic" can mean a group containing one or more rings of unsaturated cyclic carbon radicals where one or more of the carbon radicals can be replaced by one or more non-carbon radicals. An exemplary aromatic compound is benzene having a C6 ring containing three double bonds. Other exemplary aromatic compounds can include para-xylene, ortho-xylene, meta-xylene and ethylbenzene. Moreover, characterizing a stream or zone as "aromatic" can imply one or more different aromatic compounds.

As used herein, the term "support" generally means a molecular sieve that has been combined with a binder before the addition of one or more additional catalytically active components, such as a metal, or the application of a subsequent process such as reducing, sulfiding, calcining, or drying. However, in some instances, a support may have catalytic properties and can be used as a "catalyst".

As used herein, the term "non-equilibrium" generally means at least one C8 aromatic isomer can be present in a concentration that differs substantially from the equilibrium concentration at a different isomerization condition.

As used herein, the term "substantially all" is intended to indicate an amount over about 90 weight percent, preferably over about 95 weight percent, of the total amount of the referenced compound or group of compounds.

As used herein, the term "rich" is intended to indicate a concentration over about 50 weight percent, preferably over about 65 weight percent, of the referenced compound or group of compounds.

As used herein, the term "substantial absence of hydrogen" means that no free hydrogen is added to a feed mixture and that any dissolved hydrogen from prior processing is substantially less than about 0.05 moles/mole of feed, frequently less than about 0.01 moles/mole, and possibly not detectable by usual analytical methods.

DETAILED DESCRIPTION OF THE INVENTION

Figure 1:
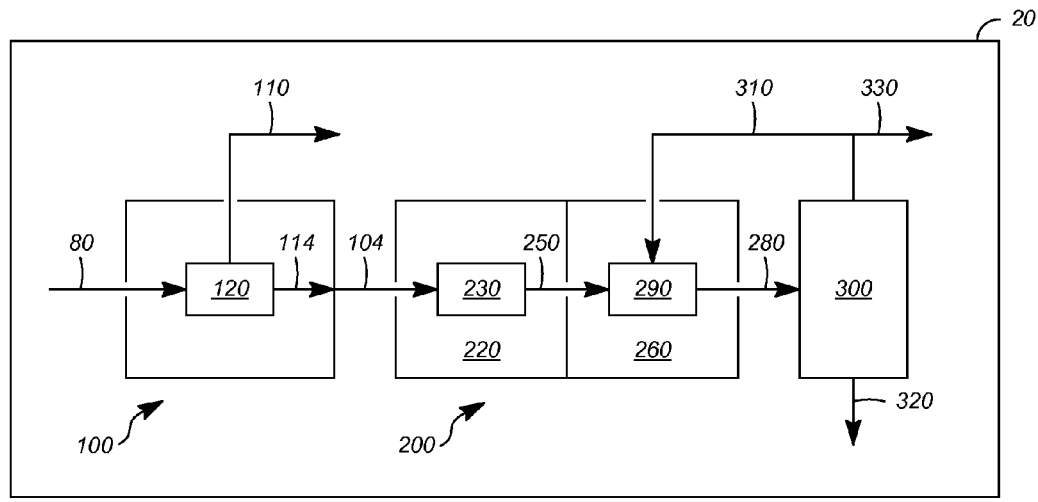
FIG. 1 is a schematic depiction of an exemplary aromatic production facility.

Referring to FIG. 1, an exemplary aromatic production facility 20 can include a xylene isomer separation zone 100, a C8 isomerization zone 200, and a separation zone 300. The aromatic production facility 20 can include other zones or units, such as an alkylation, an extractive distillation, and/or an olefin saturation zone or unit, as disclosed in, for example, U.S. Pat. No. 6,740,788 B1.

The xylene isomer, such as a para-xylene or meta-xylene, separation zone 100 can receive an alkylaromatic feed mixture in a line 80. Typically, the feed mixture may be derived from any of a variety of original sources, e.g., petroleum refining, thermal or catalytic cracking of hydrocarbons, coking of coal, or petrochemical conversions in, e.g., a refinery or petrochemical production facility. Preferably the feed mixture is found in appropriate fractions from various petroleum-refinery streams, e.g., as individual components or as certain boiling-range fractions obtained by the selective fractionation and distillation of catalytically cracked or reformed hydrocarbons.

The xylene isomer separation zone 100 can include one or more reactors 120 to produce an extract of a desired isomer, such as para-xylene, in a line 110 and a raffinate in a line 114. The xylene isomer separation zone 100 may be based on a fractional crystallization process or an adsorptive separation process. An adsorptive separation process can recover over about 99%, by weight, para-xylene in the line 110 at high recovery per pass. An exemplary xylene isomer separation zone 100 is disclosed in U.S. Pat. No. 6,740,788 B1. The raffinate, which is an effluent from the zone 100, can be sent via the line 114 and a line 104 to the C8 isomerization zone 200.

Typically, the raffinate substantially comprises the non-equilibrium alkylaromatic feed mixture in the line 104. The non-equilibrium alkylaromatic feed mixture can include isomerizable alkylaromatic hydrocarbons of the general formula $C_6H_{(6-n)}R_n$, where n is an integer of 1-5 and R is $CH_3$, $C_2H_5$, $C_3H_7$, or $C_4H_9$, in any combination suitable for isomerization to obtain at least one more valuable alkylaromatic isomer, such as para-xylene or meta-xylene, in an isomerized product. The feed mixture can include one or more ethylaromatic hydrocarbons containing at least one ethyl group, i.e., at least one R of at least one of the alkylaromatic hydrocarbons is $C_2H_5$. Suitable components of the feed mixture generally include, for example, an ethylbenzene, a meta-xylene, an ortho-xylene, a paraxylene, an ethyl-toluene, a trimethylbenzene, a diethyl-benzene, a triethylbenzene, a methylpropyl-benzene, an ethylpropylbenzene, a diisopropylbenzene, or a mixture thereof. Typically, the one or more ethylaromatic hydrocarbons are present in the feed mixture in a concentration of about 2-about 100%, by weight.

Usually the non-equilibrium mixture is prepared by removal of para-, ortho- and/or meta-xylene from a fresh C8 aromatic mixture obtained from one or more aromatic-production or aromatic-conversion processes to yield a stream depleted in at least one xylene isomer. Generally, isomerization of a non-equilibrium C8 aromatic feed mixture including xylenes and ethylbenzene to yield para-xylene is a particularly preferred application. Typically, such a mixture may have an ethylbenzene content in the approximate range of about 1-about 50%, by weight, an ortho-xylene content in the approximate range of about 0-about 35%, by weight, a meta-xylene content in the approximate range of about 0-about 95%, by weight, and a para-xylene content in the approximate range of about 0-about 30%, by weight.

The alkylaromatic-containing streams such as catalytic reformate with or without subsequent aromatic extraction can be isomerized to produce specified xylene isomers and particularly to produce para-xylene. A C8 aromatic feed may contain non-aromatic hydrocarbons, i.e., naphthenes and paraffins, in an amount up to about 30%, by weight. Preferably the isomerizable hydrocarbons consist essentially of aromatics, however, to ensure pure products from downstream recovery processes. Typically, the non-equilibrium alkylaromatic feed mixture is an effluent from a xylene isomer separation zone.

Accordingly, an alkylaromatic hydrocarbon feed mixture may be contacted sequentially with two or more catalysts respectively in a C8 isomerization zone 200 having first and second isomerization stages 220 and 260. Typically, the first isomerization stage 220 is at least for isomerizing at least one xylene and the second isomerization stage 260 is at least for isomerizing ethylbenzene. However, it should be understood that other reactions can occur in addition to isomerizing at least one xylene and ethylbenzene in respective stages 220 and 260. Contacting may be effected in either stage 220 or 260 using a fixed-bed system, a moving-bed system, a fluidized-bed system, a slurry system or an ebullated-bed system, or a batch-type operation. Preferably, a fixed-bed system is utilized in both stages 220 and 260. Each stage 220 and 260 can include, respectively, at least one reactor 230 and at least one reactor 290.

In a preferred manner, the feed mixture is preheated by suitable heating means as known in the art to the desired reaction temperature and passes in a liquid phase in the substantial absence of hydrogen into the first isomerization stage 220 containing at least one fixed reactor 230 having a first isomerization catalyst. The first isomerization stage 220 may include a single reactor 230, or two or more separate reactors with suitable measures to ensure that the desired isomerization temperature is maintained at the entrance of each reactor. The reactants may be contacted with the catalyst bed in upward-, downward-, or radial-flow fashion to obtain an intermediate stream that may contain alkylaromatic isomers in a ratio differing from the feed mixture. In the preferred processing of one or more C8 aromatics, the intermediate stream can contain xylenes in proportions closer to equilibrium than in the feed mixture plus ethylbenzene in a proportion relating to the feed mixture.

Generally, the first isomerization catalyst includes a molecular sieve, such as a zeolite. The zeolite may contain one or more metals, such as gallium and/or aluminum. Typically, the zeolite is an aluminosilicate zeolite, having a Si:$Al_2$ ratio greater than about 10, preferably greater than about 20, and a pore diameter of about 5-about 8 angstroms (Å). Specific examples of suitable zeolites are MFI, MEL, EUO, FER, MFS, MTT, MTW, TON, MOR, and FAU zeolites, as disclosed in US 2007/0004947. One exemplary MFI-type zeolite is a gallium-aluminum-MFI, with gallium and aluminum as components of the crystal structure.

The preparation of a zeolite by crystallizing a mixture including a gallium source, optionally an aluminum source, a silica source, and optionally an alkali metal source is known. Conversion of an alkali-metal-form zeolite to the hydrogen form may be performed by treatment with an aqueous solution of a mineral acid. Alternatively, hydrogen ions can be incorporated into the pentasil zeolite by ion exchange with ammonium salts such as ammonium hydroxide or ammonium nitrate followed by calcination. Desirably, an aluminosilicate zeolite can contain at least about 40%, and preferably about 40-about 46%, by weight, silicon, calculated on an elemental basis based on the molecular sieve. In addition, the aluminosilicate zeolite can contain generally about 0.5-about 7.0%, desirably about 2.0-about 5.0%, and optimally about 2.5-about 3.5%, by weight, gallium, calculated on an elemental basis based on the molecular sieve. Furthermore, the aluminosilicate zeolite can contain generally about 0.1-about 2.0%, desirably about 0.1-about 1.0%, and optimally about 0.2-about 0.4%, by weight, of another IUPAC Group 13 element, such as aluminum, calculated on an elemental basis based on the molecular sieve.

The porous microcrystalline material of the isomerization catalyst preferably is composited with a binder. The proportion of binder in the catalyst is about 5-about 90%, preferably about 10-about 70%, and optimally about 50%, by weight. The remainder can be metal and other components discussed herein. Typically, the catalyst can contain about 30-about 90%, preferably about 50%, by weight, of the aluminosilicate zeolite.

Usually catalyst particles are homogeneous with no concentration gradients of the catalyst components. Alternatively, the catalyst particles may be layered, for example, with an outer layer of a bound zeolite bonded to a relatively inert core. Examples of layered catalysts can be found in U.S. Pat. No. 6,376,730 B1 and U.S. Pat. No. 4,283,583.

The binder should be a porous, adsorptive material having a surface area of about 25-about 500 $m^2/g$ that is relatively refractory to conditions utilized in a hydrocarbon conversion process. Typically, the binder can include (1) a refractory inorganic oxide such as an alumina, a titania, a zirconia, a chromia, a zinc oxide, a magnesia, a thoria, a boria, a silica-alumina, a silica-magnesia, a chromia-alumina, an alumina-boria, or a silica-zirconia; (2) a ceramic, a porcelain, or a bauxite; (3) a silica or silica gel, a silicon carbide, a synthetically prepared or naturally occurring clay or silicate, optionally acid treated, as an example, an attapulgite clay, a diatomaceous earth, a fuller's earth, a kaolin, or a kieselguhr; (4) a crystalline zeolitic aluminosilicate, either naturally occurring or synthetically prepared, such as FAU, MEL, MFI, MOR, MTW (IUPAC Commission on Zeolite Nomenclature), in hydrogen form or in a form that has been exchanged with metal cations, (5) a spinel, such as $MgAl_2O_4$, $FeAl_2O_4$, $ZnAl_2O_4$, $CaAl_2O_4$, or a compound having a formula $MO—Al_2O_3$ where M is a metal having a valence of 2; or (6) a combination of two or more of these groups.

A preferred refractory inorganic oxide for use as a binder is an alumina. A suitable alumina material is a crystalline alumina known as a gamma-, an eta-, and a theta-alumina, with a gamma- or an eta-alumina being preferred.

The catalyst may contain a halogen component, including either fluorine, chlorine, bromine, iodine or a mixture thereof, with chlorine being preferred. Desirably, however, the catalyst contains no added halogen other than that associated with other catalyst components.

One shape for the support or catalyst can be an extrudate. Generally, the extrusion initially involves mixing of the zeolite with optionally the binder and a suitable peptizing agent to form a homogeneous dough or thick paste having the correct moisture content to allow for the formation of extrudates with acceptable integrity to withstand direct calcination. Extrudability may be determined from an analysis of the moisture content of the dough, with a moisture content in the range of about 30-about 70%, by weight, being preferred. The dough may then be extruded through a die pierced with multiple holes and the spaghetti-shaped extrudate can be cut to form particles in accordance with known techniques. A multitude of different extrudate shapes is possible, including a cylinder, a cloverleaf, a dumbbell, a trilobe, or a symmetrical or an asymmetrical polylobate. Furthermore, the dough or extrudate may be shaped to any desired form, such as a sphere, by, e.g., marumerization that can entail one or more moving plates or compressing the dough or extrudate into molds.

Alternatively, support or catalyst pellets can be formed into spherical particles by accretion methods. Such a method can entail adding liquid to a powder mixture of a zeolite and binder in a rotating pan or conical vessel having a rotating auger.

Generally, preparation of alumina-bound spheres involves dropping a mixture of molecular sieve, also, and gelling agent into an oil bath maintained at elevated temperatures. Examples of gelling agents that may be used in this process include hexamethylene tetraamine, urea, and mixtures thereof. The gelling agents can release ammonia at the elevated temperatures that sets or converts the hydrosol spheres into hydrogel spheres. The spheres may be then withdrawn from the oil bath and typically subjected to specific aging treatments in oil and an ammonia solution to further improve their physical characteristics. One exemplary oil dropping method is disclosed in U.S. Pat. No. 2,620,314.

Preferably, the resulting supports are then washed and dried at a relatively low temperature of about 50-about 200° C. and subjected to a calcination procedure at a temperature of about 450-about 700° C. for a period of about 1-about 20 hours.

Optionally, the catalyst is subjected to steaming to tailor its acid activity. The steaming may be effected at any stage of the zeolite treatment. Steaming conditions can include a water concentration of about 5-about 100%, by volume, pressure of about 100 kPa-about 2 MPa, and a temperature of about 600-about 1200° C. Preferably, the steaming temperature is about 650-about 1000° C., more preferably at least about 750° C., and optimally may be at least about 775° C. In some cases, temperatures of about 800-at least about 850° C. may be employed. The steaming should be carried out for a period of at least one hour, and periods of about 6-about 48 hours are preferred. Alternatively or in addition to the steaming, the composite may be washed with one or more solutions of an ammonium nitrate, a mineral acid, or water. The washing may be effected at any stage of the preparation, and two or more stages of washing may be employed. The catalyst can contain at least about 30%, preferably about 30-about 50%, by weight, silicon, calculated on an elemental basis based on the catalyst.

The alkylaromatic feed mixture contacts the isomerization catalyst in the liquid phase at suitable first isomerization conditions. Such conditions can include a temperature ranging from about 200-about 600° C., preferably from about 250-about 350° C. Generally, the pressure is sufficient to maintain the feed mixture in liquid phase, generally from about 500 kPa-about 5 MPa. The first isomerization stage 220 can contain a sufficient volume of catalyst to provide a liquid hourly space velocity with respect to the feed mixture of about 0.5-about 50 $hr^{-1}$, preferably about 0.5-about 20 $hr^{-1}$.

At least part of an intermediate stream in a line 250 is contacted in the second isomerization stage 260. The second isomerization stage 260 can include at least one reactor 290 having a second isomerization catalyst. At least a part of a stream rich in at least one naphthene, preferably a C8 naphthene, can be fed to the reactor 290 as well. This stream can be provided in a line 310 to the reactor 290 or combined with the intermediate stream in the line 250 and fed to the reactor 290. Thus, the intermediate stream and the stream rich in at least one naphthene can be a combined feed to the second isomerization stage 260. The stream rich in at least one naphthene will be described in greater detail hereinafter.

Desirably, the intermediate stream and/or stream rich in at least one naphthene are preheated by one or more suitable exchangers and/or heaters in the presence of a hydrogen-rich gas to the desired reaction temperature and then passed into the reactor 290. The ethylbenzene conversion catalyst can include a microcrystalline material. Such a microcrystalline material can include one or more of BEA, MTW, FAU, MCM-22, UZM-8, MOR, FER, MFI, MEL, MTT, Omega, UZM-5, TON, EUO, OFF, NU-87 and MgAPSO-31.

An exemplary zeolitic molecular-sieve component of the second isomerization catalyst can be MTW, also characterized as ZSM-12. Alternatively, the exemplary ethylbenzene catalyst can be one or more of the ATO framework types according to the ATLAS OF ZEOLITE STRUCTURE TYPES, such as the MgAPSO-31 molecular sieve as disclosed in U.S. Pat. No. 4,758,419.

The intermediate stream and/or the stream rich in naphthenes can contact the ethylbenzene conversion catalyst in the presence of hydrogen at suitable conditions. Typically, such conditions include a temperature of about 200-at least about 600° C., preferably about 300-about 500° C. Generally, the pressure is about 100 kPa-about 5 MPa, preferably less than about 3 MPa. The second isomerization stage 260 can contain a sufficient volume of catalyst to provide a liquid hourly space velocity with respect to the combined streams of about 0.5-about 50 $hr^{-1}$, preferably about 0.5-about 20 $hr^{-1}$. The intermediate stream optimally is reacted in admixture with hydrogen at a hydrogen/hydrocarbon mole ratio of about 0.5:1-about 25:1. Other inert diluents, such as nitrogen, argon, and light hydrocarbons, may be present. Exemplary conditions and catalyst for the second isomerization stage 260 are disclosed in US 2007/0004947.

The isomerized product from the second isomerization stage 260 can include a concentration of at least one alkylaromatic isomer that is higher than the equilibrium concentration at the first or second isomerization conditions. Desirably, the isomerized product in a line 280 is a mixture of one or more C8 aromatics having a concentration of para-xylene that is higher than the equilibrium concentration at the first or second isomerization conditions. The concentration of para-xylene can be at least about 24.2%, often at least about 24.4%, and may be at least about 25%, by weight. The C8 aromatic ring loss relative to the feed mixture (defined hereinafter) in the line 104 is usually less than about 2.0%, preferably less than about 1.5%.

The isomerized product in the line 280 can be fed to a separation zone 300. The separation zone 300 can be one or more distillation towers, solvent extractors, and/or mol sieve separators. An exemplary separation zone utilizing fractionation is disclosed in U.S. Pat. No. 3,835,198. The isomerized product is sent to the separation zone 300 to obtain a lighter stream containing naphthenes and a heavier stream in a line 320. Typically the heavier stream can contain xylenes and ethylbenzene. In many aromatic production facilities, this stream can be recycled back to the xylene isomer separation zone 100 after further processing, such as fractionation. The lighter stream can contain C8 naphthenes, benzene, and toluene. The benzene and toluene can be withdrawn in a line 330 as a vapor phase stream from an overhead receiver from a column in the separation zone 300, as disclosed in U.S. Pat. No. 4,783,568. The naphthenes can be sent in the line 310 to the second isomerization stage 260. The boiling point of the stream rich in at least one naphthene can be about 110-about 130° C.

The stream rich in at least one naphthene can be sent via the line 310 to the line 250 or the second stage 260, as described above. This disposition bypasses the first isomerization stage 220, improving the isomerization conversion of that stage 220. Although not wanting to be bound by theory, it is believed that the disposition of the stream rich in at least one naphthene aids in reducing C8RL by avoiding isomerizing the naphthenes primarily in the first stage 220. Such reactions can destroy C8 ringed-compounds that may help generate more xylenes. These benefits are generally unexpected due to the unpredictability of such catalyzed reactions.

Figure 2:
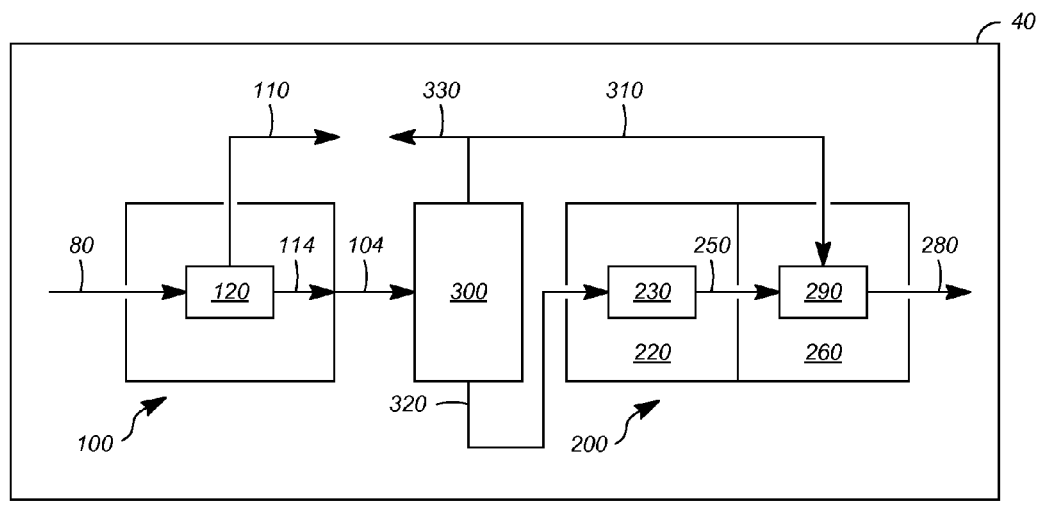
FIG. 2 is a schematic depiction of another exemplary aromatic production facility.

Referring to FIG. 2, another exemplary aromatic production facility 40 is depicted. The aromatic production facility 40 can include the xylene isomer separation zone 100, the C8 isomerization zone 200, and the separation zone 300, as discussed above. In this embodiment, the separation zone 300 can be placed before the C8 isomerization zone 200 instead of after. Thus, the non-equilibrium alkylaromatic feed mixture in the line 104 can be fed to the separation zone 300. The stream rich in at least one naphthene can be taken as, e.g., an overhead from a fractionation tower in the separation zone 300, with lighter compounds such as benzene and toluene withdrawn in the line 330. This stream can be combined with the intermediate stream in the line 250 or sent via the line 310 to the reactor 290 in the second isomerization stage 260. A stream rich in xylenes and ethylbenzene can exit the separation zone 300 through the line 320 to the C8 isomerization zone 200. This aromatic production facility 40 can achieve similar results as the aromatic production facility 20.

The elemental analysis of the catalyst components can be determined by Inductively Coupled Plasma (ICP) analysis. Some components, such as metals, can be measured by UOP Method 873-86 and other components, such as zeolite or binder where each may contain silica, or silicon can be measured by UOP Method 961-98.

All the UOP methods, such as UOP-873-86 and UOP-961-98 discussed herein, can be obtained through ASTM International, 100 Barr Harbor Drive, West Conshohocken, Pa., USA.

Illustrative Embodiments

The following examples are intended to further illustrate the subject process. These illustrations of embodiments of the invention are not meant to limit the claims of this invention to the particular details of these examples. These examples are based on engineering calculations and actual operating experience with similar processes.

Catalyst A

A gallium-aluminum substituted zeolite catalyst is prepared by making a first solution of 336.9 grams of NaOH with 989.6 grams of water. A second solution is prepared by combining 5201.1 grams of a silica source, such as a silica source sold under the trade designation of LUDOX AS-40 by E. I. Du Pont De Nemours and Company corporation of Wilmington, Del., with 5607.5 grams of water and mixing. During mixing of the second solution, 842.5 grams of an organic template, such as tetrapropylammonium bromide (50%, by weight, water solution), is added, and then the first solution is added to the second solution followed by 38.0 grams of sodium aluminate solution (LSA) and 983.6 grams of Ga(NO$_3$)$_3$ solution (8.54%, by weight, Ga$_2$O$_3$). The mixing of the combined solutions is continued until the mixture thickens and then thins to a gel. Afterwards, the gel is transferred to an autoclave and reacted for about 72 hours at a temperature of about 120-about 131° C. The solid zeolite is separated by a centrifuge and is washed 3 times.

The zeolite obtained from the autoclave is calcined in nitrogen for 2 hours and air for 10 hours at a temperature of about 560° C. After calcination, the zeolite is ammonium cation exchanged with 1.5 M NH$_4$NO$_3$ solution at about 75° C. The obtained zeolite is filtered, and ammonium cation exchanged again with the 1.5 M NH$_4$NO$_3$ solution at about 75° C. Afterwards, the zeolite is dried at 100° C. for about 12 hours to yield a zeolite containing about 3.1%, by weight, gallium and about 0.25%, by weight, aluminum based on the zeolite.

Next, about 50%, by weight, of Al$_2$O$_3$ and about 50%, by weight, of an Ga—Al-MFI zeolite are composited to form oil-dropped spheres. The spheres are dried and calcined to obtain Catalyst A.

Catalyst B

A zeolite is prepared the same as Example 1. However, about 50%, by weight, of the Al$_2$O$_3$ and about 50%, by weight, of an Ga—Al MFI zeolite are extruded to form trilobe extrudates, which are labeled Catalyst B.

Performance

The catalysts discussed above are placed in a pilot plant flow reactor. The reactor processes two non-equilibrium C8 aromatic feeds having the following approximate compositions:

TABLE 1

Feed Composition (Comparison)

| Component | Percent, By Weight |
|---|---|
| Ethylbenzene | 14 |
| Para-xylene | 1 |
| Meta-xylene | 56 |
| Ortho-xylene | 22 |
| Toluene | 1 |
| C8 naphthenes | 6 |

TABLE 2

Feed Composition

| Component | Percent, By Weight |
|---|---|
| Ethylbenzene | 15 |
| Para-xylene | 1 |
| Meta-xylene | 60 |
| Ortho-xylene | 23 |
| Toluene | 1 |

This feed in a liquid phase is contacted with each catalyst depicted below at a pressure of about 3500 kPa and a temperature of about 300° C. with no hydrogen.

The C8 ring loss or C8RL is in mole percent and defined as:

$$(1-(\text{C8 naphthenes and aromatics in product})/(\text{C8 naphthenes and aromatics in feed}))*100$$

which represents a loss of one or more C8 rings that can be converted into a desired C8 aromatic, such as para-xylene. This loss of feed generally requires more feed to be provided to generate a given amount of product, reducing the profitability of the unit. Generally, a low amount of C8RL is a favorable feature for a catalyst. The C8RL can be measured in the table below at a conversion of the following formula:

$$pX/X=[pX/(pX+mX+oX)]*100\%$$

where:

pX represents moles of para-xylene in the product;
mX represents moles of meta-xylene in the product;
oX represents moles of ortho-xylene in the product; and
X represents moles of xylene in the product.

Thus, the C8RL and a weight hourly space velocity (may be referred to as WHSV) in the table below are determined at pX/X of 23% in a product stream.

TABLE 3

| | Feed | | | |
|---|---|---|---|---|
| | Catalyst A | | Catalyst B | |
| | WHSV | C8RL | WHSV | C8RL |
| Table 1 | 15 | 1 | 9 | 0.8 |
| Table 2 | 18 | 0.6 | 10.5 | 0.45 |

As depicted above, a feed having an absence of C8 naphthenes reduces C8RL by almost by 50%. Generally, such a benefit is unexpected in view of the unpredictability of catalyzed isomerization reactions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth uncorrected in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An aromatic production facility, comprising: a C8 aromatic isomerization zone receiving a non-equilibrium alkylaromatic feed mixture and receiving a stream rich in at least one naphthene, the C8 aromatic isomerization zone comprising:

a) a first isomerization stage wherein at least a portion of the non-equilibrium alkylaromatic feed mixture is contacted at a first isomerization condition in a liquid phase in the substantial absence of hydrogen to obtain an intermediate stream; and b) a second isomerization stage wherein at least a portion of the intermediate stream and at least a portion of the stream rich in at least one naphthene are contacted at a second isomerization condition to obtain a second isomerization stage effluent with a concentration of at least one alkylaromatic isomer that is higher than a concentration of that at least one alkylaromatic isomer in the non-equilibrium alkylaromatic feed mixture;

c) a napthene rich stream providing separation zone providing at least part of the stream rich in at least one napthene; and d) a xylene isomer separation zone providing a non-equilibrium alkylaromatic stream wherein the napthene rich stream providing separation zone receives at least a portion of the non-equilibrium alkylaromatic stream to provide at least part of the stream rich in at least one naphthene and at least part of the non-equilibrium alkylaromatic feed mixture.

* * * * *